(12) United States Patent
Volgyesi

(10) Patent No.: US 10,576,241 B2
(45) Date of Patent: Mar. 3, 2020

(54) BREATH POWERED POSITIVE AIRWAY PRESSURE DEVICE

(71) Applicant: George Volgyesi, Willowdale (CA)

(72) Inventor: George Volgyesi, Willowdale (CA)

( * ) Notice: Subject to any disclaimer, the term of this patent is extended or adjusted under 35 U.S.C. 154(b) by 974 days.

(21) Appl. No.: 15/145,940

(22) Filed: May 4, 2016

(65) Prior Publication Data
US 2017/0319813 A1    Nov. 9, 2017

(51) Int. Cl.
  *A61M 16/20*    (2006.01)
  *A61M 16/08*    (2006.01)
  *A61M 16/06*    (2006.01)

(52) U.S. Cl.
  CPC ...... *A61M 16/208* (2013.01); *A61M 16/0866* (2014.02); *A61M 16/0875* (2013.01); *A61M 16/201* (2014.02); *A61M 16/06* (2013.01)

(58) Field of Classification Search
  CPC ............ A61M 16/009; A61M 16/0866; A61M 16/205; A61M 16/208; A61M 16/209; A61M 16/201; A61M 16/0875
  See application file for complete search history.

(56) References Cited

U.S. PATENT DOCUMENTS 3,216,413 A * 11/1965 Arecheta Mota ..... A61M 16/00
                                        128/205.13
5,694,926 A * 12/1997 DeVries ............... A61M 16/125
                                        128/204.21
7,506,649 B2    3/2009 Doshi et al.
2002/0104538 A1* 8/2002 Emtell ............... A61M 16/0078
                                        128/205.14
2013/0118498 A1* 5/2013 Robitaille ......... A61M 16/0075
                                        128/205.16
2014/0261425 A1    9/2014 Connor

FOREIGN PATENT DOCUMENTS

EP    2 106 819 A1    10/2009

OTHER PUBLICATIONS

Blaylock, "Immune Activation: Vaccines and the Developing Brain", The Vaccine Choice Journal, 4.1 (2017): 1-28.
White, "Auto-PEEP to Treat Obstructive Sleep Apnea", Journal of Clinical Sleep Medicine, 5.6 (2009): 538-539.
Berry et al., "A Novel Nasal Expiratory Positive Airway Pressure (EPAP) Device for the Treatment of Obstructive Sleep Apnea: A Randomized Controlled Trial", Sleep, 34.4 (2011): 479-485F.

(Continued)

*Primary Examiner* — Valerie L Woodward

(57) ABSTRACT

A breath powered positive airway pressure device having an expiratory chamber for receiving expired air from a user. The chamber has at least one resiliently flexible surface that is configured to expand to accommodate the expired air, so that the pressure within the chamber gradually increases during expiration. The device may also include an inspiratory chamber for holding air to be inspired, wherein the at least one resiliently flexible surface forms a flexible partition separating the expiratory chamber from the inspiratory chamber. The flexible partition is configured to expand into the inspiratory chamber during expiration, so that the air that is held within the inspiratory chamber also becomes pressurized during expiration.

20 Claims, 10 Drawing Sheets

(56) References Cited

OTHER PUBLICATIONS

Ginosar et al., "High Altitude, Continuous Positive Airway Pressure, and Obstructive Sleep Apnea: Subjective Observations and Objective Data", High Altitude Medicine & Biology, 14.2 (2013): 186-189.

T.S. Hakim et al., "Obstructive Sleep Apnea Treatment with EPAP Nasal Devices: Physiological Principles and Limitations", Journal of Sleep and Sleep Disorder Research, 1.1 (2017): 33-41.

Lipman et al., "Study Looking at End Expiratory Pressure for Altitude Illness Decrease (SLEEP-AID)", High Altitude Medicine & Biology, 16.2 (2015): 1-8.

Banner et al., "Effects of Expiratory Flow Resistance on Inspiratory Work of Breathing", Chest, 93.4 (1988): 795-799.

Johnson et al., "Non-Invasive Positive Pressure Ventilation during Sleep at 3800m: relationship to Acute Mountain Sickness and sleeping oxyhemoglobin saturation", Respirology, 15.2 (2010): 277-282.

Johnson et al., "Continuous Positive Airway Pressure Treatment for Acute Mountain Sickness at 4240 m in the Nepal Himalaya", High Altitude Medicine and Biology, 14.3 (2013): 230-233.

Kakkar RK, Berry RB."Positive airway pressure treatment for obstructive sleep apnea." Chest. Sep. 2007; 132 (3): 1057-72 (Abstract).

Kapil Chaudhary and Munisha Agarwal "An innovative nasal continuous positive airway pressure assembly" Indian J Crit Care Med. Mar.-Apr. 2013; 17(2): 104-106 (Abstract).

Rossi VA et al. "The effects of Provent on moderate to severe obstructive sleep apnoea during continuous positive airway pressure therapy withdrawl: a randomised controlled trial" Thorax. Sep. 2013; 68 (9): 854-9 (Abstract).

Friedman M et al. "Provent therapy for obstructive sleep apnea: Impact of nasal obstruction" Laryngoscope. Apr. 17, 2015. (Abstract).

Leon Rosenthal, M.D. et al . "A Multicenter, Prospective Study of a Novel Nasal EPAP Device in the treatment of obstructive sleep Apnea: Efficacy and 30-Day Adherence" JCSM, vol. 5, No. 6, 2009.

Peter Gay, M.D. et al., "Evaluation of Positive Airway Pressure Treatment for Sleep Related Breathing Disorders in Adults" SLEEP, vol. 29, No. 3, 2006.

Molina Healthcare "Expiratory Positive Airway Pressure (EPAP) for Obstructive Sleep Apnea".

Rajiv Doshi and Philip Westbrook "Nasal Expiratory Positive Airway Pressure (EPAP) for Treatment of Obstructive Sleep Apnea" Respiratory Therapy vol. 6 No. 4 Aug.-Sep. 2011.

Glenn Adams Nasal Expiratory Positive Airway Pressure (EPAP) Device to Treat Obstructive Sleep Apnea in Medicare Age Patients (Age >65).

Provent Product Information Sheet.

Victor Hoffstein "Review of oral appliances for treatment of sleep-disordered breathing" Sleep Breath (2007) 11:1-22.

\* cited by examiner

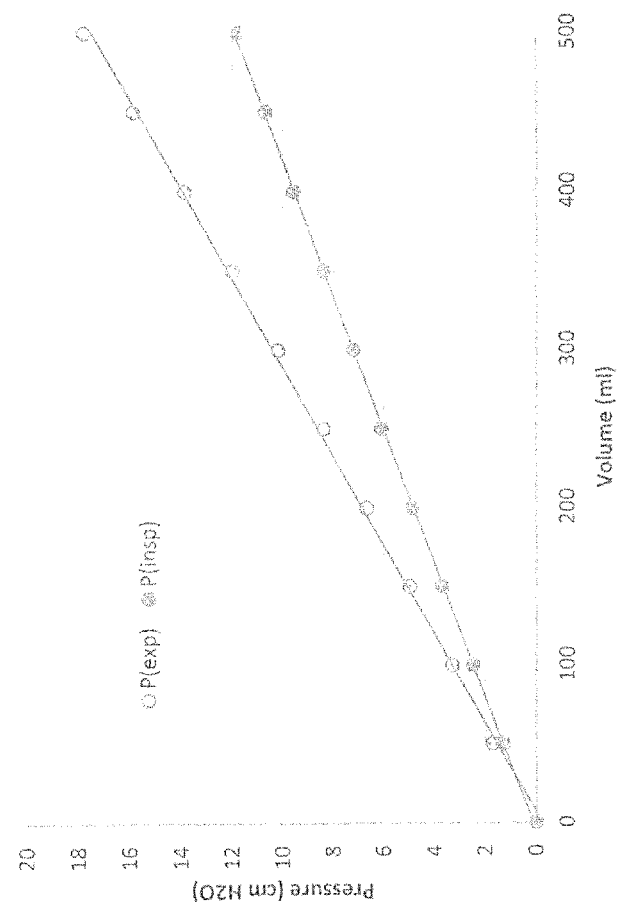

BREATH POWERED POSITIVE AIRWAY PRESSURE DEVICE

FIELD OF THE INVENTION

This invention relates to positive airway pressure devices for treating sleep apnea and other breathing conditions. More particularly, the invention provides a breath powered device that can provide positive airway pressure without requiring an external power source.

BACKGROUND OF THE INVENTION

Continuous positive airway pressure (CPAP) machines are commonly used in the treatment of obstructive sleep apnea. These machines deliver a continuous stream of air to a patient's airway, producing a positive pressure that keeps the patient's airway open and allows for unobstructed breathing. Although CPAP machines provide an effective treatment for sleep apnea, they generally require electricity to operate. As such, the long term use of these machines may be costly for patients. They may also be inoperable in situations where electricity is unavailable, such as during power outages and in remote locations.

Nasal expiratory positive airway pressure (EPAP) devices, such as Provent™ and Theravent™, provide positive airway pressure during expiration, without requiring electricity. These small, disposable devices are temporarily affixed to a user's nostrils, and incorporate vents that are designed to open while the user inhales, and to partially close while the user exhales. The increased resistance during expiration produces positive airway pressure, which may be effective in treating conditions such as sleep apnea and snoring.

These EPAP devices do not, however, provide positive airway pressure during inspiration. Nor do they allow for control of respiratory parameters such as pressure, flow and tidal volume. Furthermore, some nasal EPAP devices may produce significant airway resistance during expiration and inspiration, which increases the work of breathing and may lead to Upper Airway Resistance Syndrome (UARS). Additionally, the devices may potentially become clogged with nasal secretions, rendering them useless or even dangerous in some circumstances.

SUMMARY OF THE INVENTION

To at least partially overcome some of the disadvantages of previously known devices, the invention provides a breath powered positive airway pressure device. The device incorporates an expiratory chamber for receiving a user's expired air. The expiratory chamber has at least one resiliently flexible surface that is configured to expand to accommodate the expired air. As the expired air collects in the expiratory chamber, the flexible surface expands outwardly and the pressure within the chamber gradually increases. This pressurized air is used to provide positive airway pressure to the user.

The resiliently flexible surface permits the volume of the chamber to increase as the expired air is collected therein, so that the pressure within the chamber rises gradually. As the commencement of expiration is not restricted by high resistance, the device may allow for more comfortable and natural breathing. In preferred embodiments, the device is fully adjustable so that pressure, flow and/or volume parameters may be selected to best suit each user's individual needs. Furthermore, as the device uses the user's own breath to produce the positive airway pressure, it can be operated without requiring an external power source.

The device includes an airway connector configured to receive expired air from the user. The airway connector can optionally be in the form of a nasal pillow, a nose mask, a full-face mask, or in any other suitable form for interfacing, directly or indirectly, with the user's airway. In some embodiments of the invention, a one-way expiration valve is interposed between the airway connector and the expiratory chamber, so as to permit the expired air to pass from the airway connector to the expiratory chamber, while preventing the expired air from passing back from the expiratory chamber into the airway connector. Optionally, the one-way expiration valve may be included as part of a non-rebreathing apparatus or valve assembly.

Some embodiments of the device also include an inspiratory chamber, for delivering air to be inspired by the user. The inspiratory chamber is preferably positioned adjacent to the expiratory chamber, with the resiliently flexible surface forming a partition therebetween. This arrangement permits both the expiratory chamber and the inspiratory chamber to become pressurized, so as to provide positive airway pressure during both expiration and inspiration. In particular, when the expiratory chamber becomes pressurized during expiration, the resiliently flexible surface expands into the inspiratory chamber, compressing and pressurizing the air to be inspired that is held therein.

The device may also incorporate any desired arrangement of valves and openings for allowing the expired air to exit the device and the air to be inspired to enter the device, and for controlling or moderating flow rates and pressures within the expiratory and inspiratory chambers. For example, the device may incorporate one or more pressure control valves that release expired air from the expiratory chamber when the pressure therein exceeds a threshold pressure. These valves can be used to set maximum and minimum pressures within the chambers, so that the positive airway pressure that is provided falls within an optimized, preselected range. Preferably, the pressure control valves are adjustable so that the pressure limits can be set based on each user's individual needs.

In some embodiments of the invention, a flexible conduit connects the expiratory chamber to an air outlet, for releasing expired air from the chamber. The dimensions of the flexible conduit are selected so that the flow rate of the expired air exiting the expiratory chamber through the conduit is lower than the flow rate of expired air entering the expiratory chamber during expiration, so that the expiratory chamber becomes pressurized during expiration.

The inspiratory chamber may also have a resiliently flexible wall, with an occluder interposed between the flexible wall and the flexible conduit. During expiration, the resiliently flexible surface of the expiratory chamber expands into the inspiratory chamber, pressurizing the air to be inspired that is held therein. The increased pressure within the inspiratory chamber furthermore causes the flexible wall to expand outwards, pushing the occluder into engagement with the flexible conduit. This closes the flexible conduit, preventing the expired air from being released from the air outlet, and thus ensuring that the expiratory chamber and the inspiratory chamber remain pressurized at least at the beginning of inspiration.

During inspiration, the user draws the pressurized air from the inspiratory chamber, which reduces the pressure therein. This allows the flexible wall to retract away from the flexible conduit, disengaging the occluder from the conduit. With the conduit open, the expired air can be released from the expiratory chamber, and the pressure within the chambers can return to a baseline level before expiration begins again.

Accordingly, in at least one aspect the present invention resides in a breath powered positive airway pressure device comprising: an airway connector configured to receive expired air from a user; an expiratory chamber in fluid communication with the airway connector, for receiving the expired air therefrom, the expiratory chamber having at least one resiliently flexible surface that is configured to expand to accommodate the expired air; a one-way expiration valve interposed between the airway connector and the expiratory chamber, the one-way expiration valve permitting the expired air to pass from the airway connector to the expiratory chamber, and preventing the expired air from passing from the expiratory chamber to the airway connector; and an air outlet in fluid communication with the expiratory chamber, for releasing the expired air therefrom; wherein the air outlet is configured to release the expired air from the expiratory chamber more slowly than the expired air enters the expiratory chamber during expiration, so that the expired air within the expiratory chamber becomes pressurized during expiration.

The positive airway pressure device may further include a non-rebreathing valve assembly interposed between the airway connector and the expiratory chamber, the non-rebreathing valve assembly comprising: an expiration port in fluid communication with the expiratory chamber; the one-way expiration valve, which is interposed between the airway connector and the expiration port; an inspiration port for receiving air to be inspired by the user; and a one-way inspiration valve interposed between the airway connector and the inspiration port, the one-way inspiration valve permitting the air to be inspired to pass from the inspiration port to the airway connector, and preventing the expired air from passing from the airway connector to the inspiration port.

The positive airway pressure device may further include a pressure control valve in fluid communication with the expiratory chamber; wherein the pressure control valve is configured to open, to release some of the expired air from the expiratory chamber, when a pressure within the expiratory chamber exceeds a threshold pressure, and to close when the pressure within the expiratory chamber is at or below the threshold pressure.

Preferably, the pressure control valve is adjustable to select the threshold pressure. In some embodiments the pressure control valve is configured to maintain the pressure within the expiratory chamber at or below the threshold pressure. In some embodiments the pressure control valve is configured to maintain the pressure within the expiratory chamber at or above the threshold pressure.

The positive airway pressure device may further include an inspiratory chamber for holding the air to be inspired, the inspiratory chamber in fluid communication with the inspiration port; and a one-way air inlet valve in fluid communication with the inspiratory chamber, the one-way air inlet valve permitting the air to be inspired to enter the inspiratory chamber through the one-way air inlet valve, and preventing the air to be inspired from exiting the inspiratory chamber through the one-way air inlet valve; wherein the at least one resiliently flexible surface comprises a flexible partition separating the expiratory chamber from the inspiratory chamber, the flexible partition being configured to expand into the inspiratory chamber during expiration, so that the air to be inspired that is held within the inspiratory chamber becomes pressurized.

In some embodiments, the inspiratory chamber has a resiliently flexible wall and the positive airway pressure device further comprises: a flexible conduit interposed between, and in fluid communication with, the expiratory chamber and the air outlet; and an occluder interposed between the resiliently flexible wall and the flexible conduit; wherein the resiliently flexible wall is configured to expand toward the flexible conduit when the air to be inspired that is held within the inspiratory chamber is pressurized, so as to push the occluder into engagement with the flexible conduit, closing the flexible conduit and preventing the expired air from being released from the air outlet; and wherein the resiliently flexible wall is configured to retract away from the flexible conduit when the air to be inspired that is held within the inspiratory chamber is depressurized during inspiration, so that the occluder disengages from the flexible conduit, allowing the flexible conduit to open and permitting the expired air to be released from the air outlet.

Preferably, the expiratory chamber and the inspiratory chamber are configured so that, during a normal breathing cycle, the expiratory chamber and the inspiratory chamber are pressurized at the end of expiration and at the beginning of inspiration, and are depressurized to a baseline pressure at the end of inspiration.

In some embodiments, the positive airway pressure device is exclusively breath powered.

Optionally, the air outlet is adjustable to select a rate at which the expired air is released from the expiratory chamber; and the at least one resiliently flexible surface is adjustable to select a rate at which the pressure within the expiratory chamber increases during expiration.

In another aspect, the present invention resides in a method of providing breath powered positive airway pressure, comprising: expiring into a breath powered positive airway pressure device comprising: an airway connector configured to receive expired air from a user; an expiratory chamber in fluid communication with the airway connector, for receiving the expired air therefrom, the expiratory chamber having at least one resiliently flexible surface that is configured to expand to accommodate the expired air; a one-way expiration valve interposed between the airway connector and the expiratory chamber, the one-way expiration valve permitting the expired air to pass from the airway connector to the expiratory chamber, and preventing the expired air from passing from the expiratory chamber to the airway connector; and an air outlet in fluid communication with the expiratory chamber, for releasing the expired air therefrom; wherein the air outlet is configured to release the expired air from the expiratory chamber more slowly than the expired air enters the expiratory chamber during expiration, so that the expired air within the expiratory chamber becomes pressurized during expiration; and wherein the expiring comprises expiring into the airway connector so that the expired air within the expiratory chamber becomes pressurized and the at least one resiliently flexible surface expands.

In some embodiments, the positive airway pressure device further comprises a non-rebreathing valve assembly interposed between the airway connector and the expiratory chamber, the non-rebreathing valve assembly comprising: an expiration port in fluid communication with the expiratory chamber; the one-way expiration valve, which is interposed between the airway connector and the expiration port; an inspiration port for receiving air to be inspired by the user; and a one-way inspiration valve interposed between the airway connector and the inspiration port, the one-way inspiration valve permitting the air to be inspired to pass from the inspiration port to the airway connector, and preventing the expired air from passing from the airway connector to the inspiration port; and the method further comprises inspiring through the airway connector.

In some embodiments, the positive airway pressure device further comprises a pressure control valve in fluid communication with the expiratory chamber; wherein the pressure control valve is configured to open, to release some of the expired air from the expiratory chamber, when a pressure within the expiratory chamber exceeds a threshold pressure, and to close when the pressure within the expiratory chamber is at or below the threshold pressure; wherein the pressure control valve is adjustable to select the threshold pressure; and the method further comprises adjusting the pressure control valve to select the threshold pressure.

In some embodiments, the positive airway pressure device further comprises: an inspiratory chamber for holding the air to be inspired, the inspiratory chamber in fluid communication with the inspiration port; and a one-way air inlet valve in fluid communication with the inspiratory chamber, the one-way air inlet valve permitting the air to be inspired to enter the inspiratory chamber through the one-way air inlet valve, and preventing the air to be inspired from exiting the inspiratory chamber through the one-way air inlet valve; wherein the at least one resiliently flexible surface comprises a flexible partition separating the expiratory chamber from the inspiratory chamber, the flexible partition being configured to expand into the inspiratory chamber during expiration, so that the air to be inspired that is held within the inspiratory chamber becomes pressurized; and the expiring comprises expiring into the airway connector so that the expired air within the expiratory chamber becomes pressurized and the flexible partition expands into the inspiratory chamber, thereby pressurizing the air to be inspired that is held within the inspiratory chamber; and the inspiring comprises inspiring, through the airway connector, the pressurized air that is held within the inspiratory chamber.

In some embodiments, the inspiratory chamber has a resiliently flexible wall and the positive airway pressure device further comprises: a flexible conduit interposed between, and in fluid communication with, the expiratory chamber and the air outlet; and an occluder interposed between the resiliently flexible wall and the flexible conduit; wherein the resiliently flexible wall is configured to expand toward the flexible conduit when the air to be inspired that is held within the inspiratory chamber is pressurized, so as to push the occluder into engagement with the flexible conduit, closing the flexible conduit and preventing the expired air from being released from the air outlet; wherein the resiliently flexible wall is configured to retract away from the flexible conduit when the air to be inspired that is held within the inspiratory chamber is depressurized during inspiration, so that the occluder disengages from the flexible conduit, allowing the flexible conduit to open and permitting the expired air to be released from the air outlet; and the expiring comprises expiring into the airway connector so that the expired air within the expiratory chamber becomes pressurized and the flexible partition expands into the inspiratory chamber, thereby pressurizing the air to be inspired that is held within the inspiratory chamber and causing the resiliently flexible wall to push the occluder into engagement with the flexible conduit, closing the flexible conduit and preventing the expired air from being released from the air outlet; and the inspiring comprises inspiring, through the airway connector, the pressurized air that is held within the inspiratory chamber so that the resiliently flexible wall retracts away from the flexible conduit, so that the occluder disengages from the flexible conduit, allowing the flexible conduit to open and permitting the expired air to be released from the air outlet.

In some embodiments, the inspiring further comprises allowing a sufficient volume of the expired air to be released from the air outlet so that the expiratory chamber and the inspiratory chamber are depressurized to a baseline pressure at the end of the inspiration.

In some embodiments, the expiring comprises expiring into the airway connector, while sleeping, to treat obstructive sleep apnea; and the inspiring comprises inspiring through the airway connector, while sleeping, to treat obstructive sleep apnea.

In some embodiments, the air outlet is adjustable to select a rate at which the expired air is released from the expiratory chamber; and the at least one resiliently flexible surface is adjustable to select a rate at which the pressure within the expiratory chamber increases during expiration; and the method further comprises: adjusting the air outlet to select the rate at which the expired air is released from the expiratory chamber; and adjusting the at least one resiliently flexible surface to select the rate at which the pressure within the expiratory chamber increases during expiration.

The inventor has appreciated that, in at least some preferred embodiments of the invention, the device can be operated without external power; can provide adjustable positive airway pressure at least during the beginning of inspiration and the end of expiration; does not produce excessive resistance or otherwise impede peak expiratory flow at the commencement of expiration; provides low flow resistance during both inspiration and expiration; is reusable without limit; has no components requiring disposal or refill; and is safe and effective.

BRIEF DESCRIPTION OF THE DRAWINGS

Further aspects and advantages of the invention will appear from the following description taken together with the accompanying drawings, in which:

FIG. 10 shows a plot of the relationship between pressure and volume in the expiratory chamber and the inspiratory chamber of the device of FIG. 7.

DETAILED DESCRIPTION OF THE DRAWINGS

Figure 1:
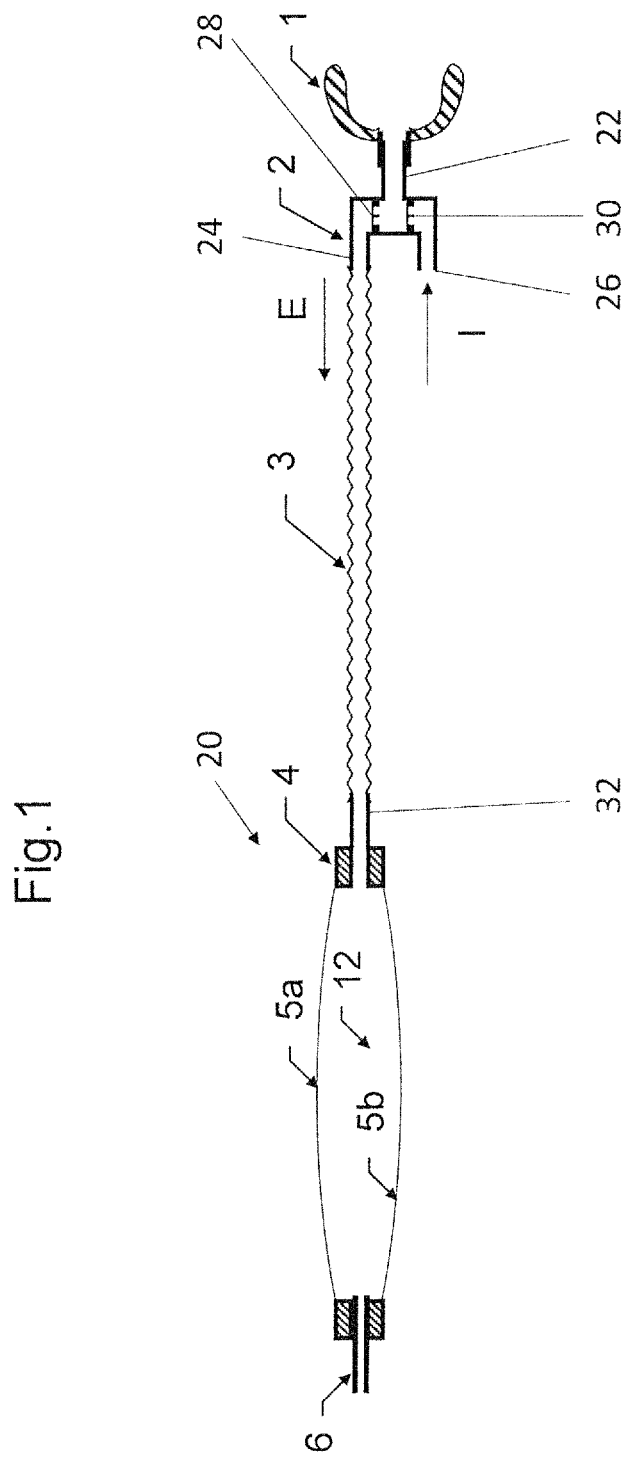
FIG. 1 shows a schematic cross-sectional view of a positive airway pressure device in accordance with a first preferred embodiment of the invention.

FIG. 1 shows a positive airway pressure device 20 in accordance with a first preferred embodiment of the invention. The device 20 includes an airway connector 1 for conveying air to and from a user's airway, a non-rebreathing valve assembly 2 in fluid communication with the airway connector 1, and a corrugated hose 3 attaching the non-rebreathing valve 2 to an expiratory chamber 12.

The airway connector 1 preferably forms a relatively fluid tight seal around the user's nose and/or mouth, so that most or all of the air that is inhaled and exhaled by the user passes therethrough. The airway connector 1 may, for example, be in the form of a nasal pillow or mask.

The non-rebreathing valve assembly 2 has an airway port 22 that connects to the airway connector 1; an expiration port 24 that connects to the corrugated hose 3; and an inspiration port 26 that is open to the external environment. A one-way expiration valve 28 is interposed between the airway port 22 and the expiration port 24; and a one-way inspiration valve 30 is interposed between the airway port 22 and the inspiration port 26. The one-way expiration valve 28 is configured to allow air to pass from the airway port 22 to the expiration port 24, and to prevent air from passing from the expiration port 24 to the airway port 22. The one-way inspiration valve 30 is configured to allow air to pass from the inspiration port 26 to the airway port 22, and to prevent air from passing from the airway port 22 to the inspiration port 26. This arrangement ensures that all of the user's expired air passes through the expiration port 24 and into the expiratory chamber 12, and all of the user's inspired air is drawn from the external environment via the inspiration port 26. The flow direction of the expired air exiting the non-rebreathing valve assembly 2 and the inspired air entering the non-rebreathing valve assembly 2 are depicted in FIG. 1 by arrows labelled as E and I, respectively.

The corrugated hose 3 provides a conduit for delivering the expired air from the expiration port 24 to the expiratory chamber 12. The corrugated hose 3 is flexible and stretchable, so as to permit the user to move relative to the expiratory chamber 12 while using the device 20.

The expiratory chamber 12 is defined by an annular frame 4 with two resiliently flexible membranes 5a, 5b stretched across each side of the frame 4. An expired air inlet 32 connects the expiratory chamber 12 to the corrugated hose 3, and an expired air outlet 6 releases the expired air into the external environment. The expired air outlet 6 provides a relatively narrow conduit, so that, during expiration, expired air is released from the expired air outlet 6 more slowly than it is received by the expired air inlet 32. This causes the expired air to collect within the expiratory chamber 12 during expiration, so that the pressure within the chamber 12 increases.

To moderate this pressure increase, the resiliently flexible membranes 5a, 5b are configured to expand or bulge outwards as the expired air collects within the chamber 12. This increases the volume of the chamber 12, so that the pressure within the chamber 12 increases more gradually than it otherwise would if the volume remained fixed. The resilient or elastic properties of the membranes 5a, 5b cause them to return to their flat, unexpanded state as the pressure within the chamber 12 returns to equilibrium with the outside environment.

The device 20 is configured so that the user is able to breathe comfortably, with breathing parameters such as tidal volume, pressure and flow rate that are clinically acceptable. For example, the size of the expiratory chamber 12, the flexibility of the membranes 5a, 5b, and the diameters of the expired air inlet 32 and the expired air outlet 6 are selected so that an acceptable volume of air can be expired therethrough at an acceptable flow rate, without requiring excessive breathing effort.

Optionally, various components of the device 20 can be made adjustable, so that the device 20 can be optimized to suit the particular clinical needs and comfort preferences of each individual user. For example, an adjustment mechanism could be used to tighten or loosen the membranes 5a, 5b, so as to alter the rate at which the pressure within the chamber 12 increases during expiration. The expired air outlet 6 could also be made adjustable, to control the rate at which the expired air is released therefrom.

To operate the device 20, the airway connector 1 is sealed against the user's nose and/or mouth. Any desired mechanism can be used to hold the connector 1 in place, such as a strap or adhesive. The user then breathes through the connector 1. During inspiration, air is drawn from the environment via the inspiration port 26 of the non-rebreathing valve assembly 2. The one-way expiration valve 28 prevents the user from inspiring air from the expiratory chamber 12. During expiration, the expired air is directed through the non-rebreathing valve assembly 2 and the corrugated hose 3 into the expiratory chamber 12. The one-way inspiration valve 30 prevents the expired air from exiting the device 20 through the inspiration port 26.

As the expired collects within the chamber 12, the membranes 5a, 5b expand outwardly, increasing the volume of the chamber 12. This causes the pressure within the chamber 12 to rise gradually during expiration. The increased pressure within the chamber 12 during expiration provides positive pressure to the patient's airway. This positive airway pressure may be used, for example, to treat obstructive sleep apnea.

During inspiration, at least some of the expired air is released from the expiratory chamber 12 via the expired air outlet 6, reducing the pressure within the chamber 12. The rate at which the expired air is released from the expired air outlet 6 may be selected so that, during a normal breathing cycle, the pressure within the chamber 12 returns to equilibrium with the external environment prior to the commencement of each expiration. Alternatively, the device 20 could be configured so that, during a normal breathing cycle, the chamber 12 does not reach equilibrium with the external environment prior to the commencement of each expiration, but rather maintains a baseline positive pressure. When configured in this way, the device 20 is able to provide at least some positive airway pressure at the very beginning of the user's expiration.

The inventor has appreciated that the device 20 is able to provide positive airway pressure during expiration, without requiring an external power source. The device 20 can also be configured to provide a gradual increase in pressure during expiration, so that the user can breathe comfortably while using the device 20.

Figure 2:
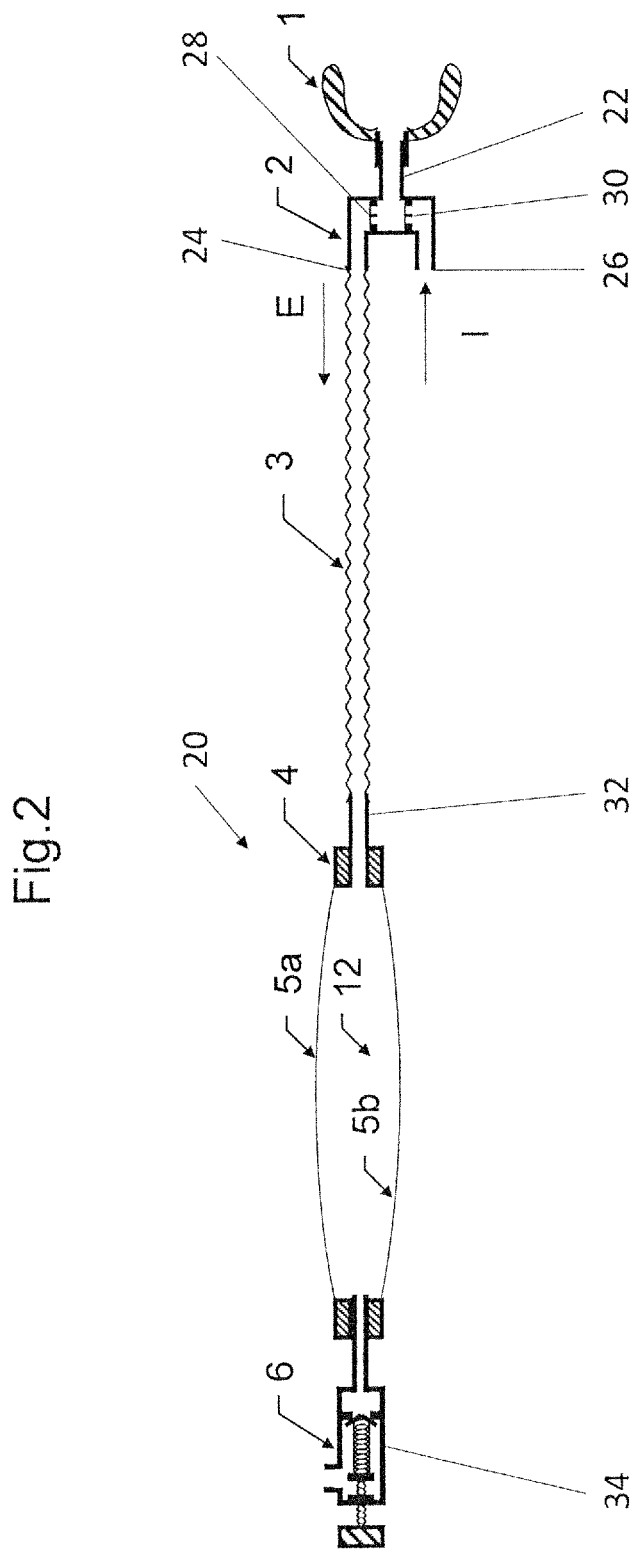
FIG. 2 shows a schematic cross-sectional view of a positive airway pressure device in accordance with a second preferred embodiment of the invention.

A positive airway pressure device 20 in accordance with a second preferred embodiment of the invention is shown in FIG. 2, wherein like numerals are used to denote like components. The device 20 shown in FIG. 2 is identical to the embodiment shown in FIG. 1, with the exception that the expired air outlet 6 now includes an adjustable pressure control valve 34. The pressure control valve 34 is configured to open, to release expired air from the chamber 12, when the pressure within the chamber 12 exceeds a preselected threshold pressure. When the pressure within the chamber 12 is at or below the threshold pressure, the pressure control valve 34 closes.

In this embodiment of the invention, the pressure control valve 34 can be used to control the pressure within the chamber 12. As the pressure control valve 34 provides the only opening through which the expired air is able to exit the expiratory chamber 12, once the chamber 12 is initially pressurized by the user's first expiration, the pressure within the chamber 12 will thereafter remain positive. This configuration of the device 20 ensures that at least a minimum positive airway pressure is provided during the user's entire expiration.

Optionally, the expired air outlet 6 can be configured so that, while the pressure control valve 34 is open, the expired air is released from the chamber 12 more slowly than it is received by the expired air inlet 32, with the result that pressure within the chamber 12 rises above the threshold pressure during expiration. During inspiration, expired air would be released from the chamber 12 until the threshold pressure was reached, at which point the pressure control valve 34 would close. This would allow the device 20 to provide a gradual increase in pressure, similar to the first embodiment described above, while also maintaining a minimum positive airway pressure at the beginning of expiration.

Alternatively, the expired air outlet 6 could be configured to release expired air from the chamber 12 very quickly when the pressure control valve 34 opens. This would prevent the pressure within the chamber 12 from rising significantly above the threshold pressure during normal expiration. This configuration would allow the device 20 to provide a relatively uniform positive airway pressure during expiration.

The pressure control valve 34 is adjustable so as to allow the user, or the user's healthcare professional, to select the threshold pressure at which the valve 34 opens. Optionally, the valve 34 is also adjustable to select the rate at which the expired air is released when the valve 34 is open. By adjusting these parameters, the device 20 can be configured in accordance with each individual user's comfort preferences and/or clinical needs.

Figure 3:
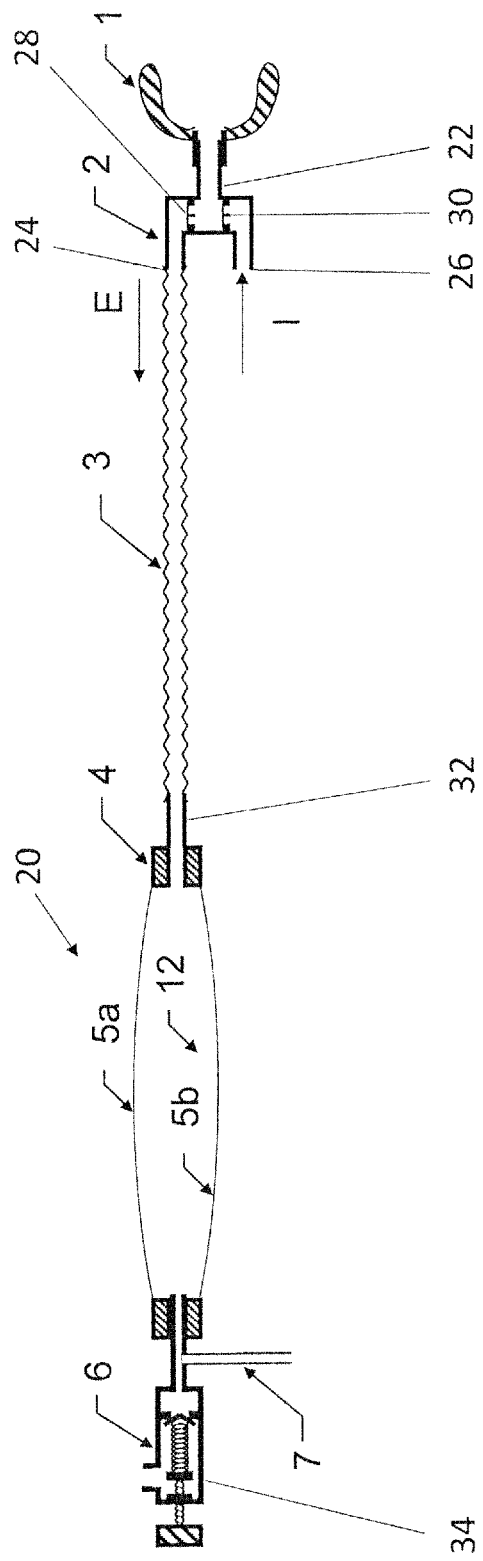
FIG. 3 shows a schematic cross-sectional view of a positive airway pressure device in accordance with a third preferred embodiment of the invention.

A positive airway pressure device 20 in accordance with a third preferred embodiment of the invention is shown in FIG. 3, wherein like numerals are used to denote like components. The device 20 shown in FIG. 3 is identical to the embodiment shown in FIG. 2, with the exception that the expired air outlet 6 additionally includes a leak tube 7, which is located between the chamber 12 and the pressure control valve 34.

The leak tube 7 permits expired air to exit the chamber 12, even when the pressure control valve 34 is closed. In this configuration, the pressure control valve 34 is used to set a maximum pressure within the chamber 12. In particular, the pressure control valve 34 can be configured to rapidly release expired air from the chamber 12 when the threshold pressure is reached, thereby preventing the pressure within the chamber 12 from rising significantly above the threshold pressure. The leak tube 7 is configured to release expired air from the chamber 12 more slowly.

This configuration allows the device 20 to provide a gradual rise in pressure during expiration, similar to the first embodiment, while also setting a maximum pressure. By setting a maximum pressure, it is possible to avoid applying excessive positive pressure to the user's airway, which could cause discomfort or otherwise interfere with normal breathing. As in the previously described embodiment, the valve 34 is adjustable so that the user, or the user's healthcare professional, can set the threshold pressure as desired.

Figure 4:
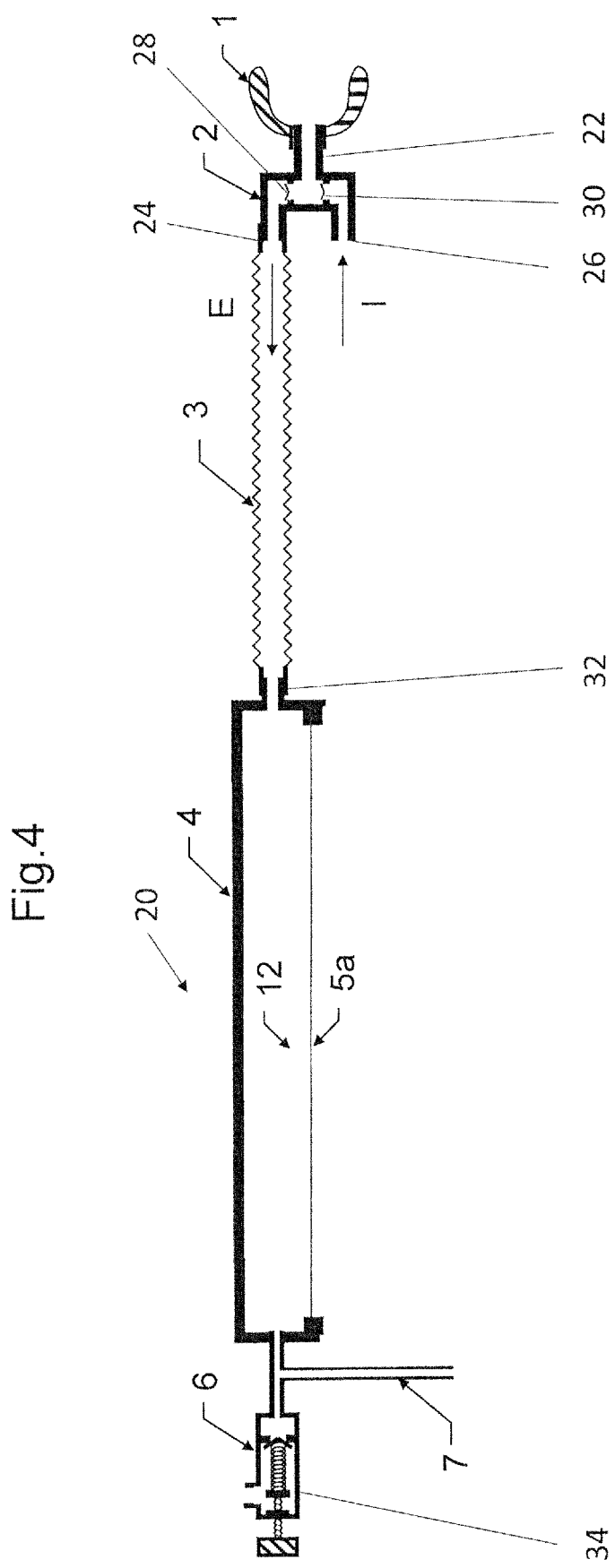
FIG. 4 shows a schematic cross-sectional view of a positive airway pressure device in accordance with a fourth preferred embodiment of the invention.

A positive airway pressure device 20 in accordance with a fourth preferred embodiment of the invention is shown in FIG. 4, wherein like numerals are used to denote like components. The device 20 shown in FIG. 4 is generally identical to the embodiment shown in FIG. 3, with the exception that one side of the frame 4 is provided with a rigid side wall, in place of the resiliently flexible membrane 5b. This flat, rigid surface makes it easier to stably rest the chamber 12 on a bedside table or the like when in use. Otherwise, the device 20 operates in an identical manner to the third embodiment as described above.

Figure 5:
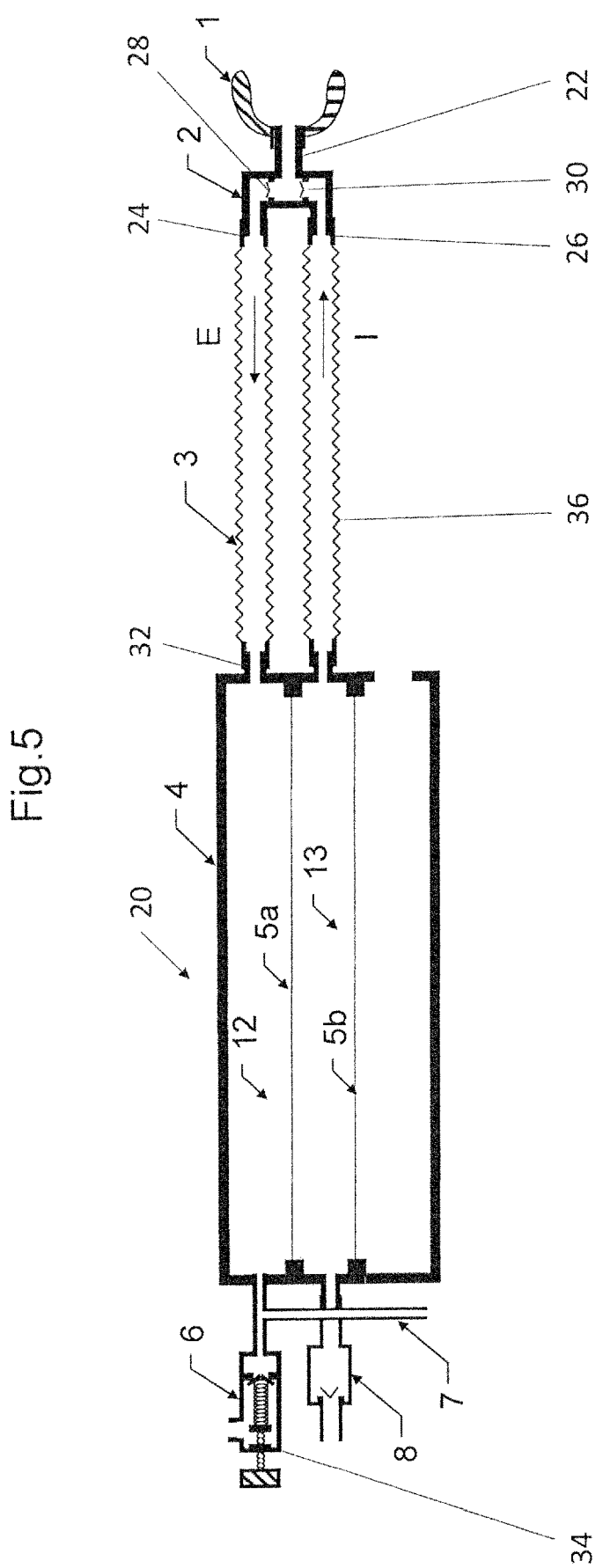
FIG. 5 shows a schematic cross-sectional view of a positive airway pressure device in accordance with a fifth preferred embodiment of the invention, showing an expiratory chamber and an inspiratory chamber in a depressurized state.
Figure 6:
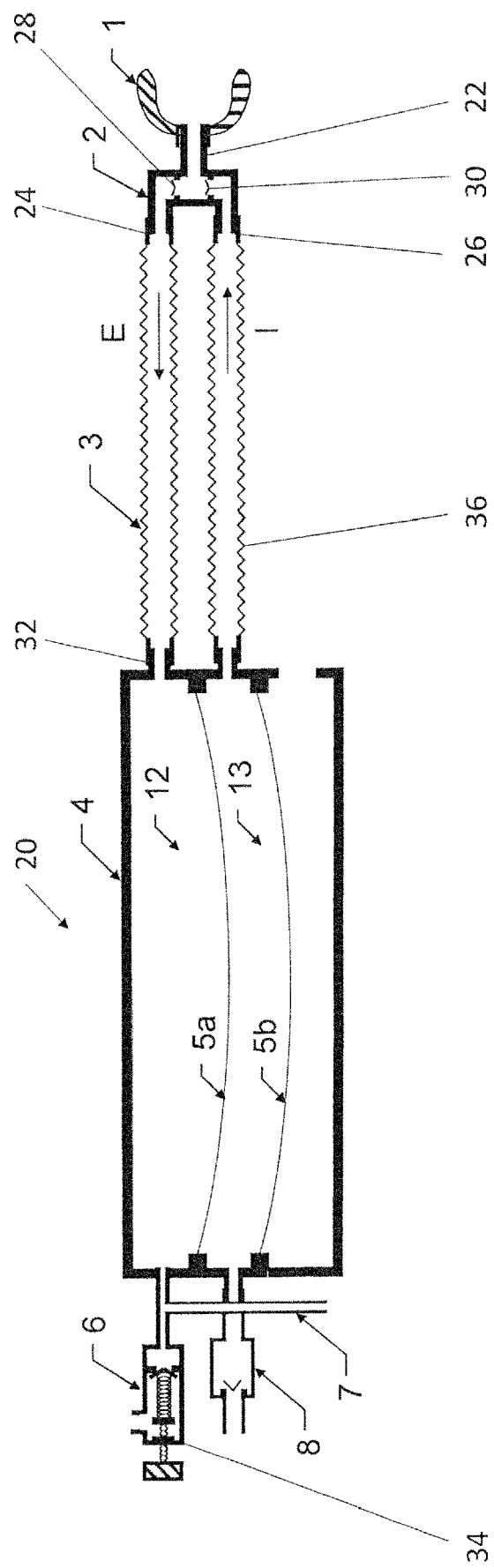
FIG. 6 shows a schematic cross-sectional view of the positive airway pressure device of FIG. 5, showing the expiratory chamber and the inspiratory chamber in a pressurized state.

A positive airway pressure device 20 in accordance with a fifth preferred embodiment of the invention is shown in FIGS. 5 and 6, wherein like numerals are used to denote like components. In this embodiment of the device 20, the frame 4 is in the form of a short, rigid cylinder, with the expiratory chamber 12 defined between the resiliently flexible membrane 5a and a side wall of the frame 4.

The frame 4 also contains an inspiratory chamber 13 for holding air to be inspired by the user. The inspiratory chamber 13 is defined between the resiliently flexible membrane 5a and the resiliently flexible membrane 5b, and is connected to the inspiration port 26 by a second corrugated hose 36. The inspiratory chamber 13 receives the air to be inspired from the external environment via a low resistance one-way air inlet valve 8.

As in the previously described embodiments, to operate the device 20, the user breathes through the airway connector 1. The expired air is directed through the non-rebreathing valve assembly 2 and the corrugated hose 3 into the expiratory chamber 12. The leak tube 7 is configured to release expired air from the chamber 12 more slowly than it is received by the expired air inlet 32, such that the pressure within the chamber 12 increases during expiration.

As in the previously described embodiments, the flexible membrane 5a expands outward to increase the volume of the expiratory chamber 12 and accommodate the expired air that is received, as shown in FIG. 6. However, unlike in the previously described embodiments, in this embodiment the flexible membrane 5a forms a partition between the expiratory chamber 12 and the inspiratory chamber 13, such that the flexible membrane 5a also expands into the inspiratory chamber 13, decreasing the volume thereof. This causes the pressure in both the expiratory chamber 12 and the inspiratory chamber 13 to increase.

As in the previously described embodiments, the pressurization of the expiratory chamber 12 provides positive airway pressure to the user during expiration. In addition, in this embodiment the pressurization of the inspiratory chamber 13 also provides positive airway pressure at least at the beginning of inspiration.

During inspiration, the user initially draws pressurized air from the inspiratory chamber 13 via the airway connector 1. As the air is drawn from the chamber 13, the pressure within the chamber 13 decreases. Once the pressure within the chamber 13 reaches the same pressure as the external environment, additional air may be drawn through the low resistance one-way air inlet valve 8.

Expired air is released from the expiratory chamber 12 via the leak tube 7 during inspiration, so that the pressure within the expiratory chamber 12 returns to a baseline level, and the flexible membrane 5a returns to its flat, unexpanded state as shown in FIG. 5. This permits the inspiratory chamber 13 to return to its initial volume before getting compressed and pressurized again during the next expiration.

Figure 7:
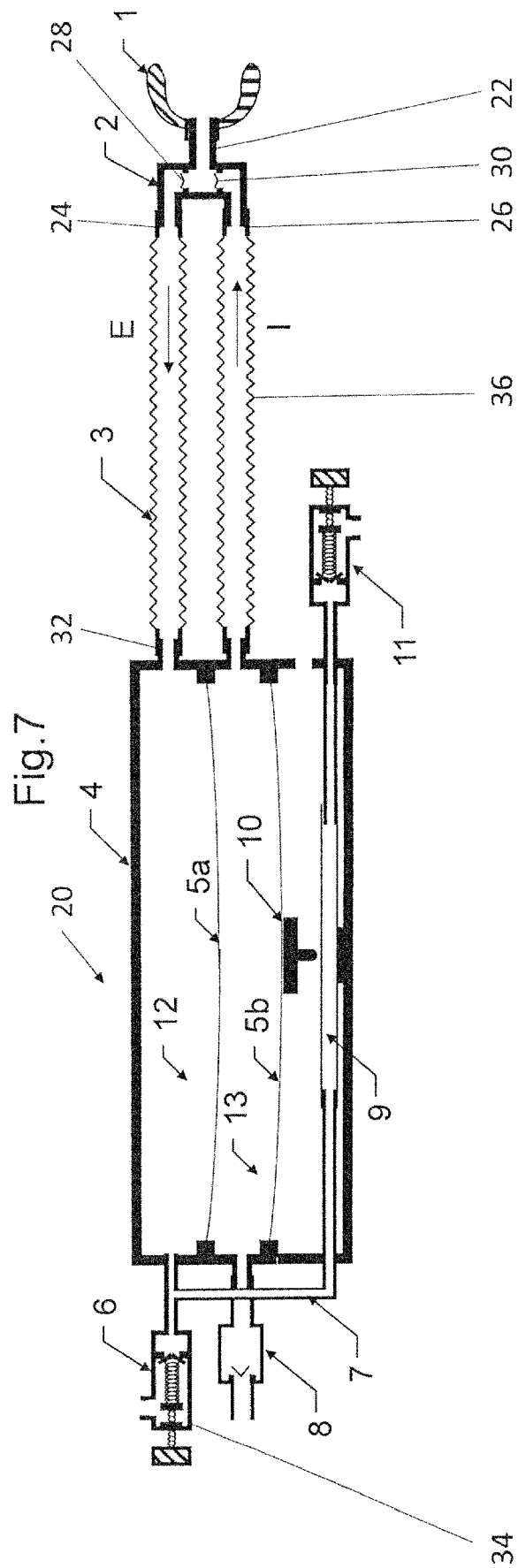
FIG. 7 shows a schematic cross-sectional view of a positive airway pressure device in accordance with a sixth preferred embodiment of the invention, showing an expiratory chamber and an inspiratory chamber in a depressurized state.
Figure 8:
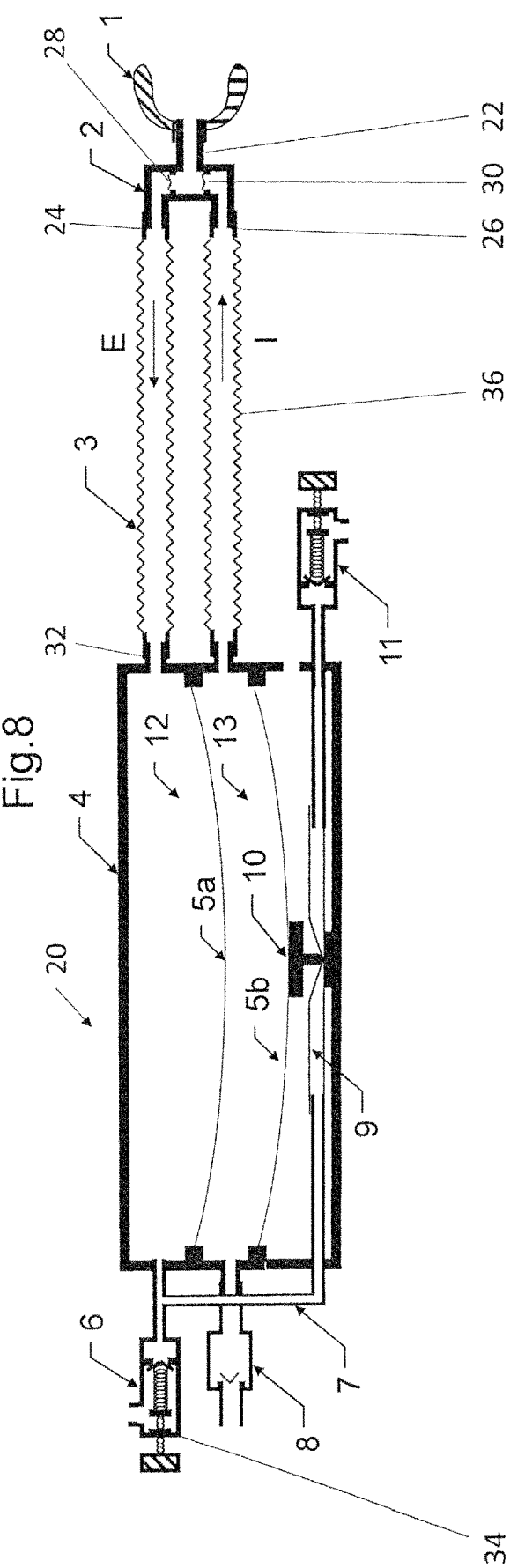
FIG. 8 shows a schematic cross-sectional view of the positive airway pressure device of FIG. 7, showing the expiratory chamber and the inspiratory chamber in a pressurized state.

A positive airway pressure device 20 in accordance with a sixth preferred embodiment of the invention is shown in FIGS. 7 and 8, wherein like numerals are used to denote like components. The device 20 shown in FIGS. 7 and 8 is generally identical to the embodiment shown in FIGS. 5 and 6, with the exception that an additional valve assembly is included for controlling the release of expired air from the expiratory chamber 12.

In this embodiment of the invention, the leak tube 7 includes a flexible section 9 positioned inside the frame 4, as well as a second pressure control valve 11. The pressure control valve 11 is used to set a minimum pressure within the expiratory chamber 12, in much the same way as in the second embodiment described above. The device 20 also includes an occluder 10, which is fixed to the bottom surface of the flexible membrane 5b.

During operation of the device 20, the user's expired air collects within the expiratory chamber 12. This causes the flexible membrane 5a to expand into the inspiratory chamber 13, pressurizing the air contained therein. The increased pressure within the chamber 13 furthermore causes the membrane 5b to expand outwardly, pushing the occluder 10 into engagement with the flexible section 9 of the leak tube 7, as shown in FIG. 8.

The engagement of the occluder 10 with the flexible section 9 closes the leak tube 7, preventing the release of expired air from the expiratory chamber 12 through the leak tube 7. This ensures that the expiratory chamber 12 and the inspiratory chamber 13 remain pressurized during the entire expiration, even if the rate at which expired air enters the expiratory chamber 12 decreases at the end of expiration. The pressure control valve 34 ensures that the pressure within the chamber 12 does not exceed a pre-selected maximum pressure, as in the previously described embodiments.

At the beginning of inspiration, the engagement of the occluder 10 with the flexible section 9 of the leak tube 7 ensures that the inspiratory chamber 13 is pressurized. As the pressurized air is drawn from the inspiratory chamber 13 through the corrugated hose 36, the pressure within the chamber 13 decreases. This causes the flexible membrane 5b to retract away from the flexible section 9, pulling the occluder 10 out of engagement with the flexible section 9. This opens the leak tube 7, allowing expired air to escape from the expiratory chamber 12, and decreasing the pressure therein. Once a baseline minimum pressure is reached, the pressure control valve 11 closes.

The device 20 is configured so that the expiratory chamber 12 reaches the minimum baseline pressure by the end of a normal inspiration, allowing the expiratory chamber 12 and the inspiratory chamber 13 to return to their baseline volumes and pressures before the next expiration begins.

Figure 9:
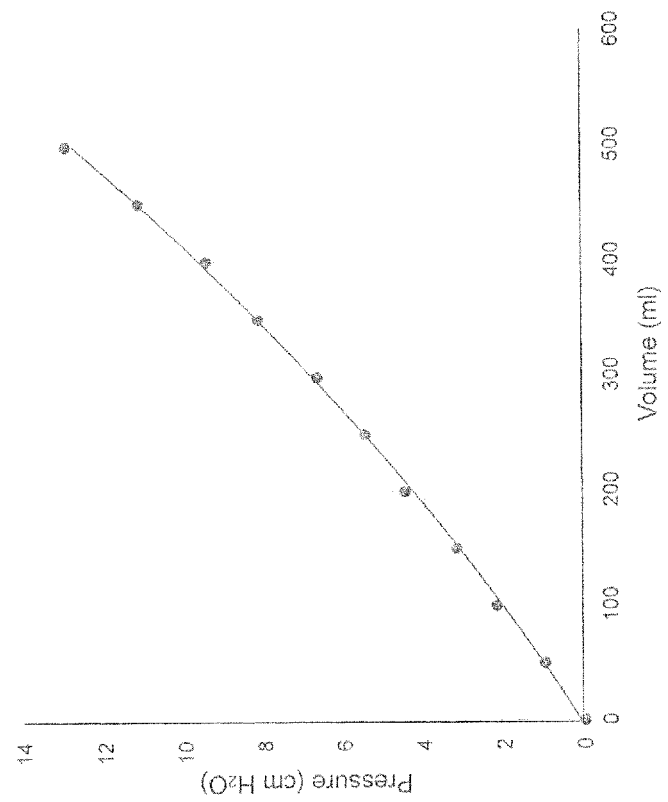
FIG. 9 shows a plot of the relationship between pressure and volume in an expiratory chamber of the device of FIG. 1.

The relationship between pressure and volume in the inspiratory chamber 13 and the expiratory chamber 12 is shown in FIG. 10. This curve was obtained by monitoring pressure within the chambers 12, 13 during stepwise inflation, with all outlets blocked. The relationship between pressure and volume depends on the diameter of the flexible membranes 5a, 5b and the magnitude of their stretch. In general, the larger the diameter of the membranes 5a, 5b, the smaller the incremental increase in pressure during stepwise inflation. The tighter the membranes 5a, 5b are stretched, the higher the incremental pressure rise inside the chambers 12, 13. The diameter and stretch properties of the membranes 5a, 5b may be selected or adjusted to provide the desired pressure rise in response to a normal tidal volume. The relationship between pressure and volume in the expiratory chamber 12 of the device 20 shown in FIG. 1 is depicted in FIG. 9.

In some embodiments of the invention, the chambers 12, 13 and their stretched membranes 5a, 5b may be modelled by electric capacitors. In particular, the higher the volume (charge), the higher the pressure (voltage). Furthermore, the combination of the two chambers 12 and 13 may be modelled by the series combination of two capacitors.

It will be understood that, although various features of the invention have been described with respect to one or another of the embodiments of the invention, the various features and embodiments of the invention may be combined or used in conjunction with other features and embodiments of the invention as described and illustrated herein.

Although the preferred embodiments described above show the device 20 as including a non-rebreathing valve assembly 2, it is to be appreciated that this valve assembly 2 is not strictly necessary. For example, in embodiments of the device 20 where positive airway pressure is provided only during expiration, and where the airway connector 1 interfaces only with the user's nose, the device 20 could be designed so that the user expires into the airway connector 1, and inspires directly from the external environment through the user's mouth. In such embodiments, a non-rebreathing valve assembly 2 would not be strictly required to operate the device 20.

It is to be appreciated that the device 20 need not have the specific size, shape, and configuration as shown in the exemplary embodiments. Rather, any shape or construction that provides positive airway pressure in a functionally equivalent or analogous manner could be used as desired.

The airway connector 1 could have any suitable construction for transporting air to and from the user's airway, including for example a nose pillow, a nose mask, or a full face mask. The airway connector 1 could also be adapted to interface indirectly with the user's airway. For example, for patients who breathe through a breathing tube, the airway connector 1 could be adapted to connect to the breathing tube.

Although the device 20 has been described above as receiving air to be inspired from the external environment, it is to be appreciated that the device 20 could be adapted to receive air from any desired source. For example, the device 20 could receive air from a humidifier or an oxygenated source, if desired. The device 20 could also be configured to deliver the expired air to another apparatus, rather than releasing it into the external environment. For example, the expired air could be collected by an apparatus that measures tidal volume, $O_2$ and $CO_2$ concentrations, or other parameters.

The flexible membranes 5a, 5b could be made from any suitable materials that provide the desired flexibility and resiliency, including natural and synthetic materials such as rubbers, elastomers, latex, polyisoprene, polychloroprene and the like.

The one-way inspiration valve 30, the one-way expiration valve 28, the low resistance one-way air inlet valve 8, and the pressure control valves 6 and 11 could have any desired construction suitable to provide control of air flow and/or pressure, including for example ball valves, diaphragm valves, duckbill valves, and the like. The pressure control valves 6 and 11 could include disposable or reusable positive end-expiratory pressure (PEEP) valves.

The corrugated hoses 3 and 36 could be replaced with any suitable conduits for transporting air to the expiratory chamber 12 and from the inspiratory chamber 13, including for example non-corrugated tubes with any suitable diameter, length, and degree of flexibility.

It is to be appreciated that, in some embodiments, the device 20 may incorporate features that require electricity to operate. For example, the device 20 could incorporate sensors and a display for recording and displaying information about the operation of the device 20, such as tidal volume, pressure, and other parameters. The device 20 could also incorporate a generator for converting some of the mechanical energy of the user's breathing into electricity, for powering such features.

Although this disclosure has described and illustrated certain preferred embodiments of the invention, it is to be understood that the invention is not restricted to these particular embodiments. Rather, the invention includes all embodiments which are functional or mechanical equivalents of the specific embodiments and features that have been described and illustrated herein.

The invention claimed is:

1. A breath powered positive airway pressure device comprising:
   an airway connector configured to receive expired air from a user;
   an expiratory chamber in fluid communication with the airway connector, for receiving the expired air therefrom, the expiratory chamber having a rigid frame and at least one resiliently flexible surface stretched over the rigid frame, wherein the at least one resiliently flexible surface is configured to expand to accommodate the expired air;
   a one-way expiration valve interposed between the airway connector and the expiratory chamber, the one-way expiration valve permitting the expired air to pass from the airway connector to the expiratory chamber, and preventing the expired air from passing from the expiratory chamber to the airway connector; and
   an air outlet in fluid communication with the expiratory chamber, for releasing the expired air therefrom;
   wherein the air outlet is configured to release the expired air from the expiratory chamber more slowly than the expired air enters the expiratory chamber during expiration, so that the expired air within the expiratory chamber becomes pressurized during expiration, and
   wherein the at least one resiliently flexible surface is adjustable to select a rate at which the pressure within the expiratory chamber increases during expiration.

2. The positive airway pressure device according to claim 1, further comprising a non-rebreathing valve assembly interposed between the airway connector and the expiratory chamber, the non-rebreathing valve assembly comprising:
   an expiration port in fluid communication with the expiratory chamber;
   the one-way expiration valve, which is interposed between the airway connector and the expiration port;
   an inspiration port for receiving air to be inspired by the user; and
   a one-way inspiration valve interposed between the airway connector and the inspiration port, the one-way inspiration valve permitting the air to be inspired to pass from the inspiration port to the airway connector, and preventing the expired air from passing from the airway connector to the inspiration port.

3. The positive airway pressure device according to claim 2, further comprising:
   an inspiratory chamber for holding the air to be inspired, the inspiratory chamber in fluid communication with the inspiration port; and
   a one-way air inlet valve in fluid communication with the inspiratory chamber, the one-way air inlet valve permitting the air to be inspired to enter the inspiratory chamber through the one-way air inlet valve, and preventing the air to be inspired from exiting the inspiratory chamber through the one-way air inlet valve;
   wherein the at least one resiliently flexible surface comprises a flexible partition separating the expiratory chamber from the inspiratory chamber, the flexible partition being configured to expand into the inspiratory chamber during expiration, so that the air to be inspired that is held within the inspiratory chamber becomes pressurized.

4. The positive airway pressure device according to claim 3, wherein the inspiratory chamber has a resiliently flexible wall;
   the positive airway pressure device further comprising:
   a flexible conduit interposed between, and in fluid communication with, the expiratory chamber and the air outlet; and
   an occluder interposed between the resiliently flexible wall and the flexible conduit;
   wherein the resiliently flexible wall is configured to expand toward the flexible conduit when the air to be inspired that is held within the inspiratory chamber is pressurized, so as to push the occluder into engagement with the flexible conduit, closing the flexible conduit and preventing the expired air from being released from the air outlet; and
   wherein the resiliently flexible wall is configured to retract away from the flexible conduit when the air to be inspired that is held within the inspiratory chamber is depressurized during inspiration, so that the occluder disengages from the flexible conduit, allowing the flexible conduit to open and permitting the expired air to be released from the air outlet.

5. The positive airway pressure device according to claim 3, wherein the expiratory chamber and the inspiratory chamber are configured so that, during a normal breathing cycle, the expiratory chamber and the inspiratory chamber are pressurized at the end of expiration and at the beginning of inspiration, and are depressurized to a baseline pressure at the end of inspiration.

6. The positive airway pressure device according to claim 1, further comprising a pressure control valve in fluid communication with the expiratory chamber;
   wherein the pressure control valve is configured to open, to release some of the expired air from the expiratory chamber, when a pressure within the expiratory chamber exceeds a threshold pressure, and to close when the pressure within the expiratory chamber is at or below the threshold pressure.

7. The positive airway pressure device according to claim 6, wherein the pressure control valve is adjustable to select the threshold pressure, and the pressure control valve is configured to maintain the pressure within the expiratory chamber at or below the threshold pressure.

8. The positive airway pressure device according to claim 1, wherein the device is exclusively breath powered, and the air outlet is adjustable to select a rate at which the expired air is released from the expiratory chamber.

9. A method of providing breath powered positive airway pressure, comprising:
expiring into a breath powered positive airway pressure device comprising:
an airway connector configured to receive expired air from a user;
an expiratory chamber in fluid communication with the airway connector, for receiving the expired air therefrom, the expiratory chamber having a rigid frame and at least one resiliently flexible surface stretched over the rigid frame, wherein the at least one resiliently flexible surface is configured to expand to accommodate the expired air, wherein the at least one resiliently flexible surface is adjustable to select a rate at which the pressure within the expiratory chamber increases during expiration;
a one-way expiration valve interposed between the airway connector and the expiratory chamber, the one-way expiration valve permitting the expired air to pass from the airway connector to the expiratory chamber, and preventing the expired air from passing from the expiratory chamber to the airway connector; and
an air outlet in fluid communication with the expiratory chamber, for releasing the expired air therefrom, wherein the air outlet is adjustable to select a rate at which the expired air is released from the expiratory chamber;
wherein the air outlet is configured to release the expired air from the expiratory chamber more slowly than the expired air enters the expiratory chamber during expiration, so that the expired air within the expiratory chamber becomes pressurized during expiration;
wherein the expiring comprises expiring into the airway connector so that the expired air within the expiratory chamber becomes pressurized and the at least one resiliently flexible surface expands, and
wherein the method further comprises:
adjusting the air outlet to select the rate at which the expired air is released from the expiratory chamber; and
adjusting the at least one resiliently flexible surface to select the rate at which the pressure within the expiratory chamber increases during expiration.

10. The method according to claim 9, wherein the positive airway pressure device further comprises a non-rebreathing valve assembly interposed between the airway connector and the expiratory chamber, the non-rebreathing valve assembly comprising:
an expiration port in fluid communication with the expiratory chamber;
the one-way expiration valve, which is interposed between the airway connector and the expiration port;
an inspiration port for receiving air to be inspired by the user; and
a one-way inspiration valve interposed between the airway connector and the inspiration port, the one-way inspiration valve permitting the air to be inspired to pass from the inspiration port to the airway connector, and preventing the expired air from passing from the airway connector to the inspiration port;
the method further comprising inspiring through the airway connector.

11. The method according to claim 10, wherein the positive airway pressure device further comprises:
an inspiratory chamber for holding the air to be inspired, the inspiratory chamber in fluid communication with the inspiration port; and
a one-way air inlet valve in fluid communication with the inspiratory chamber, the one-way air inlet valve permitting the air to be inspired to enter the inspiratory chamber through the one-way air inlet valve, and preventing the air to be inspired from exiting the inspiratory chamber through the one-way air inlet valve;
wherein the at least one resiliently flexible surface comprises a flexible partition separating the expiratory chamber from the inspiratory chamber, the flexible partition being configured to expand into the inspiratory chamber during expiration, so that the air to be inspired that is held within the inspiratory chamber becomes pressurized;
wherein the expiring comprises expiring into the airway connector so that the expired air within the expiratory chamber becomes pressurized and the flexible partition expands into the inspiratory chamber, thereby pressurizing the air to be inspired that is held within the inspiratory chamber; and
wherein the inspiring comprises inspiring, through the airway connector, the pressurized air that is held within the inspiratory chamber.

12. The method according to claim 11, wherein the inspiratory chamber has a resiliently flexible wall;
the positive airway pressure device further comprising:
a flexible conduit interposed between, and in fluid communication with, the expiratory chamber and the air outlet; and
an occluder interposed between the resiliently flexible wall and the flexible conduit;
wherein the resiliently flexible wall is configured to expand toward the flexible conduit when the air to be inspired that is held within the inspiratory chamber is pressurized, so as to push the occluder into engagement with the flexible conduit, closing the flexible conduit and preventing the expired air from being released from the air outlet;
wherein the resiliently flexible wall is configured to retract away from the flexible conduit when the air to be inspired that is held within the inspiratory chamber is depressurized during inspiration, so that the occluder disengages from the flexible conduit, allowing the flexible conduit to open and permitting the expired air to be released from the air outlet;
wherein the expiring comprises expiring into the airway connector so that the expired air within the expiratory chamber becomes pressurized and the flexible partition expands into the inspiratory chamber, thereby pressurizing the air to be inspired that is held within the inspiratory chamber and causing the resiliently flexible wall to push the occluder into engagement with the flexible conduit, closing the flexible conduit and preventing the expired air from being released from the air outlet; and
wherein the inspiring comprises inspiring, through the airway connector, the pressurized air that is held within the inspiratory chamber so that the resiliently flexible wall retracts away from the flexible conduit, so that the occluder disengages from the flexible conduit, allowing the flexible conduit to open and permitting the expired air to be released from the air outlet.

13. The method according to claim 12, wherein the inspiring further comprises allowing a sufficient volume of the expired air to be released from the air outlet so that the expiratory chamber and the inspiratory chamber are depressurized to a baseline pressure at the end of the inspiration.

14. The method according to claim 13, wherein the expiring comprises expiring into the airway connector, while sleeping, to treat obstructive sleep apnea; and
wherein the inspiring comprises inspiring through the airway connector, while sleeping, to treat obstructive sleep apnea.

15. The method according to claim 9, wherein the positive airway pressure device further comprises a pressure control valve in fluid communication with the expiratory chamber;
wherein the pressure control valve is configured to open, to release some of the expired air from the expiratory chamber, when a pressure within the expiratory chamber exceeds a threshold pressure, and to close when the pressure within the expiratory chamber is at or below the threshold pressure;
wherein the pressure control valve is adjustable to select the threshold pressure;
the method further comprising adjusting the pressure control valve to select the threshold pressure.

16. A breath powered positive airway pressure device comprising:
an airway connector configured to receive expired air from a user;
an expiratory chamber in fluid communication with the airway connector, for receiving the expired air therefrom, the expiratory chamber having a rigid frame and at least one resiliently flexible surface stretched over the rigid frame, wherein the at least one resiliently flexible surface is configured to expand to accommodate the expired air;
a non-rebreathing valve assembly interposed between the airway connector and the expiratory chamber, the non-rebreathing valve assembly comprising:
an expiration port in fluid communication with the expiratory chamber;
a one-way expiration valve interposed between the airway connector and the expiration port, the one-way expiration valve permitting the expired air to pass from the airway connector to the expiratory chamber, and preventing the expired air from passing from the expiratory chamber to the airway connector;
an inspiration port for receiving air to be inspired by the user; and
a one-way inspiration valve interposed between the airway connector and the inspiration port, the one-way inspiration valve permitting the air to be inspired to pass from the inspiration port to the airway connector, and preventing the expired air from passing from the airway connector to the inspiration port; and
an inspiratory chamber for holding the air to be inspired, the inspiratory chamber in fluid communication with the inspiration port, wherein the inspiratory chamber has a resiliently flexible wall;
a one-way air inlet valve in fluid communication with the inspiratory chamber, the one-way air inlet valve permitting the air to be inspired to enter the inspiratory chamber through the one-way air inlet valve, and preventing the air to be inspired from exiting the inspiratory chamber through the one-way air inlet valve;
an air outlet in fluid communication with the expiratory chamber, for releasing the expired air therefrom;
a flexible conduit interposed between, and in fluid communication with, the expiratory chamber and the air outlet; and
an occluder interposed between the resiliently flexible wall and the flexible conduit;
wherein the air outlet is configured to release the expired air from the expiratory chamber more slowly than the expired air enters the expiratory chamber during expiration, so that the expired air within the expiratory chamber becomes pressurized during expiration;
wherein the at least one resiliently flexible surface comprises a flexible partition separating the expiratory chamber from the inspiratory chamber, the flexible partition being configured to expand into the inspiratory chamber during expiration, so that the air to be inspired that is held within the inspiratory chamber becomes pressurized;
wherein the resiliently flexible wall is configured to expand toward the flexible conduit when the air to be inspired that is held within the inspiratory chamber is pressurized, so as to push the occluder into engagement with the flexible conduit, closing the flexible conduit and preventing the expired air from being released from the air outlet; and
wherein the resiliently flexible wall is configured to retract away from the flexible conduit when the air to be inspired that is held within the inspiratory chamber is depressurized during inspiration, so that the occluder disengages from the flexible conduit, allowing the flexible conduit to open and permitting the expired air to be released from the air outlet.

17. The positive airway pressure device according to claim 16, further comprising a pressure control valve in fluid communication with the expiratory chamber;
wherein the pressure control valve is configured to open, to release some of the expired air from the expiratory chamber, when a pressure within the expiratory chamber exceeds a threshold pressure, and to close when the pressure within the expiratory chamber is at or below the threshold pressure.

18. The positive airway pressure device according to claim 17, wherein the pressure control valve is adjustable to select the threshold pressure, and the pressure control valve is configured to maintain the pressure within the expiratory chamber at or below the threshold pressure.

19. The positive airway pressure device according to claim 16, wherein the expiratory chamber and the inspiratory chamber are configured so that, during a normal breathing cycle, the expiratory chamber and the inspiratory chamber are pressurized at the end of expiration and at the beginning of inspiration, and are depressurized to a baseline pressure at the end of inspiration.

20. The positive airway pressure device according to claim 16, wherein the device is exclusively breath powered, and the air outlet is adjustable to select a rate at which the expired air is released from the expiratory chamber.

* * * * *